United States Patent
Mbata

(10) Patent No.: US 10,653,324 B1
(45) Date of Patent: May 19, 2020

(54) WRIST WORN CARBON MONOXIDE DETECTOR

(71) Applicant: Kelechi Ignatius Mbata, Somerset, NJ (US)

(72) Inventor: Kelechi Ignatius Mbata, Somerset, NJ (US)

(*) Notice: Subject to any disclaimer, the term of this patent is extended or adjusted under 35 U.S.C. 154(b) by 0 days.

(21) Appl. No.: 16/601,995

(22) Filed: Oct. 15, 2019

Related U.S. Application Data

(63) Continuation of application No. 16/563,835, filed on Sep. 7, 2019.

(51) Int. Cl.
| | |
|---|---|
| *A61B 5/0205* | (2006.01) |
| *A61B 5/1455* | (2006.01) |
| *A61B 5/00* | (2006.01) |
| *G01N 33/00* | (2006.01) |
| *G01N 33/48* | (2006.01) |
| *A61B 5/024* | (2006.01) |
| *A61B 5/08* | (2006.01) |

(52) U.S. Cl.
CPC ........ *A61B 5/0205* (2013.01); *A61B 5/14551* (2013.01); *A61B 5/681* (2013.01); *A61B 5/7425* (2013.01); *G01N 33/004* (2013.01); *G01N 33/0063* (2013.01); *G01N 33/0075* (2013.01); *G01N 33/48* (2013.01); *A61B 5/02438* (2013.01); *A61B 5/082* (2013.01); *A61B 5/6831* (2013.01); *A61B 2560/0242* (2013.01)

(58) Field of Classification Search
CPC ... A61B 5/0205; A61B 5/14551; A61B 5/681; A61B 5/7425; A61B 5/02438; A61B 5/082; A61B 5/6831; A61B 2560/0242; G01N 33/004; G01N 33/0063; G01N 33/0075; G01N 33/48
See application file for complete search history.

(56) References Cited

U.S. PATENT DOCUMENTS

| | | | |
|---|---|---|---|
| 6,744,373 | B2 | 6/2004 | Koyano |
| 8,107,920 | B2 | 1/2012 | Ayed |
| D664,880 | S | 8/2012 | Cobbett |
| 2004/0085213 | A1 | 5/2004 | Weng |
| 2006/0250261 | A1 | 11/2006 | Henrie |
| 2015/0212057 | A1 | 7/2015 | Darveau |
| 2018/0231515 | A1 | 8/2018 | Voumard |

FOREIGN PATENT DOCUMENTS

WO    WO 2017/025791 A1    2/2017

*Primary Examiner* — Lindsey G Wehrheim
(74) *Attorney, Agent, or Firm* — Walter J. Tencza, Jr.

(57) ABSTRACT

An apparatus including a band; and a first device configured to attach to a person's wrist using the band; wherein the first device includes a first carbon monoxide level detector; wherein the first device includes a housing and a second device configured to be moved with respect to the housing from a first state to a second state; wherein in the first state a person cannot blow into the second device and cause a carbon monoxide level of the person's breath to be detected by the first carbon monoxide level detector; and wherein in the second state the person can blow into the second device and cause a carbon monoxide level of the person's breath to be detected by the first carbon monoxide level detector. The first device may include a second carbon monoxide level detector which is configured to detect a carbon monoxide level in ambient air.

20 Claims, 4 Drawing Sheets

Fig. 1A
Fig. 1B
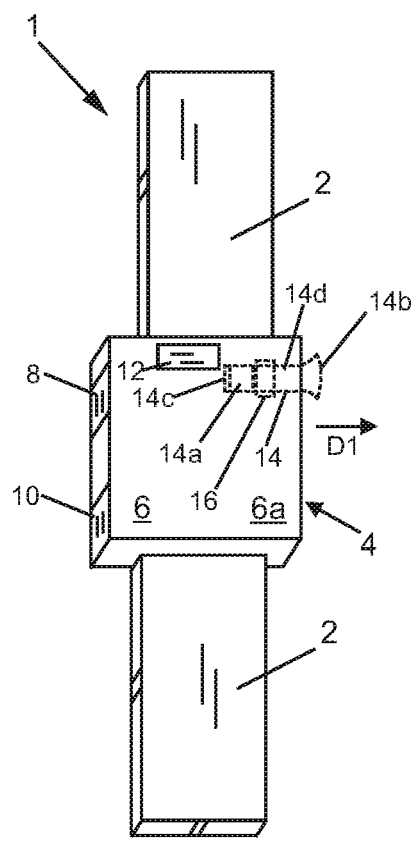
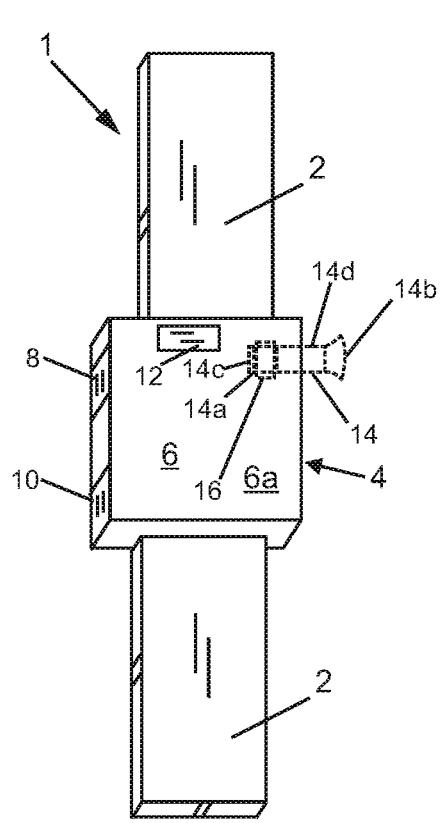

Fig. 2A
Fig. 2B
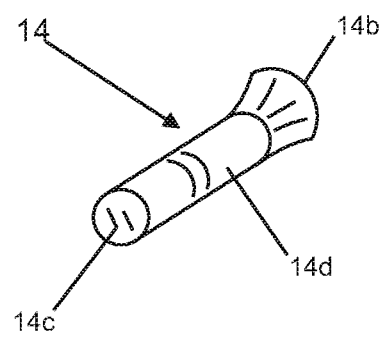
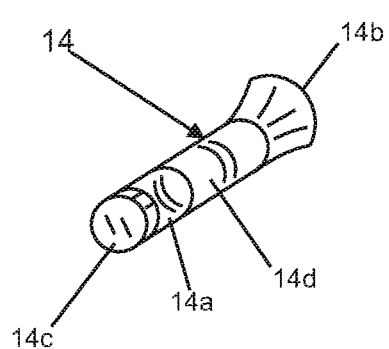

Fig. 4A
Fig. 4B
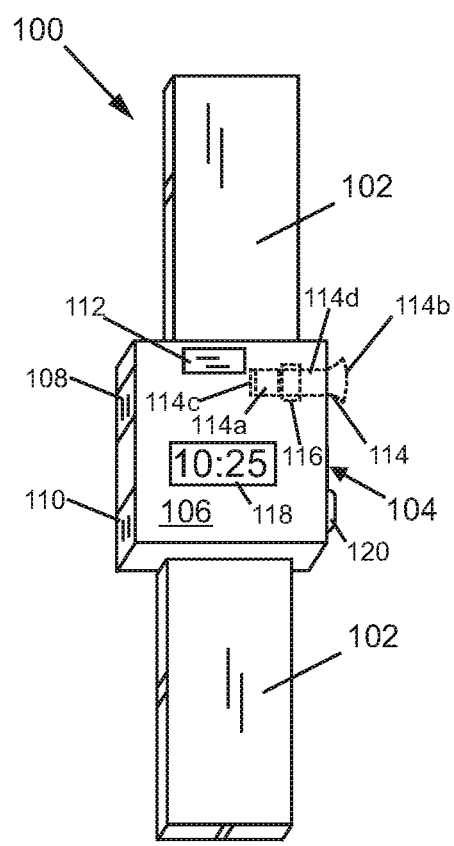
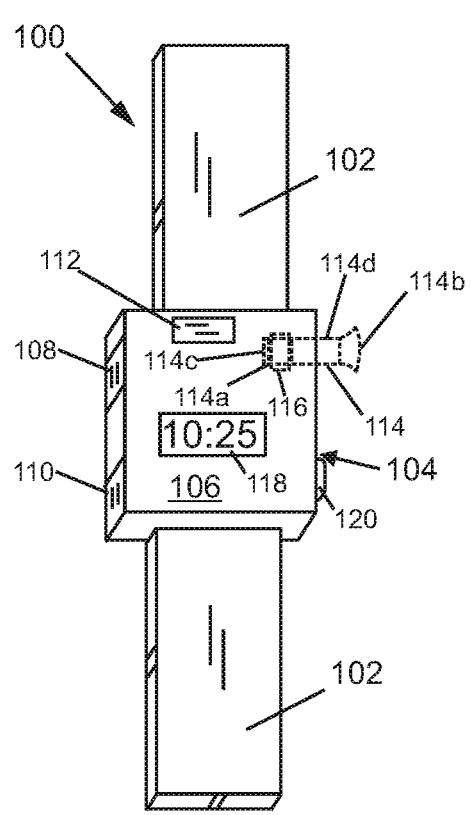

WRIST WORN CARBON MONOXIDE DETECTOR

CROSS REFERENCE TO RELATED APPLICATION(S)

The present application is a continuation of and claims the priority of U.S. patent application Ser. No. 16/563,835, titled "WRIST WORN CARBON MONOXIDE DETECTOR", filed on Sep. 7, 2019, inventor and applicant Kelechi Ignatius Mbata.

FIELD OF THE INVENTION

This invention relates to wrist worn detectors, such as smart watches.

BACKGROUND OF THE INVENTION

Generally, wearable technology providing various functions, such as various Apple (trademarked) watches are known in the art.

SUMMARY OF THE INVENTION

In at least one embodiment, a wrist worn carbon monoxide detector is provided which may in the form of a wrist watch or a bracelet. The detector may be configured and/or programmed to alert a user when carbon monoxide (CO) is detected.

In at least one embodiment, an apparatus is provided comprising a band; and a first device configured to attach to a person's wrist using the band; wherein the first device includes a first carbon monoxide level detector; wherein the first device includes a housing and a second device configured to be moved with respect to the housing from a first state to a second state; wherein in the first state a person cannot blow into the second device and cause a carbon monoxide level of the person's breath to be detected by the first carbon monoxide level detector; and wherein in the second state the person can blow into the second device and cause a carbon monoxide level of the person's breath to be detected by the first carbon monoxide level detector.

The first device may include a second carbon monoxide level detector which is configured to detect a carbon monoxide level in ambient air. The first device may include a computer display which is configured to display a carbon monoxide level of the person's breath detected by the first carbon monoxide level detector. The first device may include a computer display which is configured to display a carbon monoxide level of the person's breath detected by the first carbon monoxide level detector; and the computer display may also be configured to display a carbon monoxide level in ambient air detected by the second carbon monoxide detector.

In at least one embodiment, the first device may include a heart rate monitor and/or an SpO2 (peripheral capillary oxygen saturation) detector.

In at least one embodiment, a method is provided comprising attaching a first device to a person's wrist by a band; and moving a second device with respect to a housing of the first device, from a first state to a second state; wherein the first device includes a first carbon monoxide level detector; wherein in the first state a person cannot blow into the second device and cause a carbon monoxide level of the person's breath to be detected by the first carbon monoxide level detector; and wherein in the second state the person can blow into the second device and cause a carbon monoxide level of the person's breath to be detected by the first carbon monoxide level detector. The first device may be configured as previously specified.

BRIEF DESCRIPTION OF THE DRAWINGS

FIG. 1A shows a top, front, and left perspective view of an apparatus in accordance with an embodiment of the present invention, with the apparatus shown in a first state;

FIG. 1B shows a top, front, and left perspective view of the apparatus of FIG. 1A shown in a second state;

FIG. 2A shows a top, left, and front perspective view of a tube having a handle for use with the apparatus of FIG. 1A;

FIG. 2B shows a bottom, left, and rear perspective view of the tube having the handle of FIG. 2A;

FIG. 4A shows a top, front, and left perspective view of another apparatus in accordance with an embodiment of the present invention, with the apparatus of FIG. 3A shown in a third state; and FIG. 4B shows a top, front, and left perspective view of the apparatus of FIG. 3A shown in a fourth state.

DETAILED DESCRIPTION OF THE DRAWINGS

Figure 3:
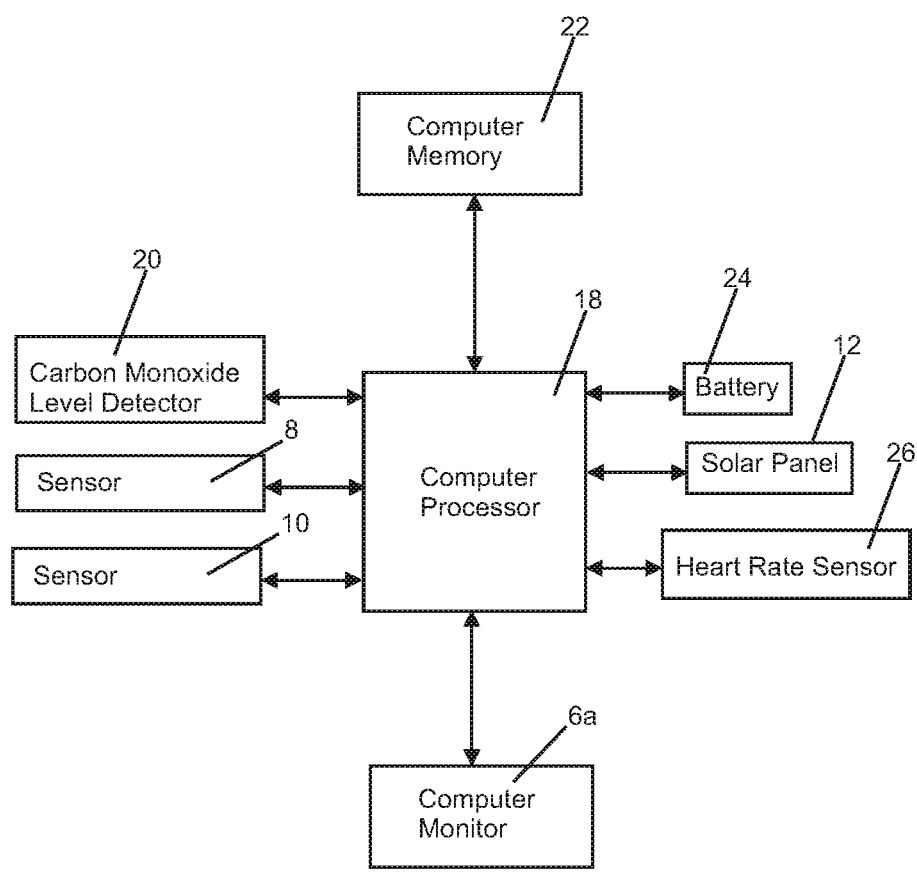
FIG. 3 is a block diagram of components of the apparatus of FIG. 1A.

FIG. 1A shows a top, front, and left perspective view of an apparatus 1 in accordance with an embodiment of the present invention, with the apparatus 1 shown in a first state. The apparatus 1 may in the form of a bracelet, and may include a device 4 attached to a band 2.

The device 4 may include a housing 6 to which a sensor 8 and a sensor 10 are attached and/or integrated with. The device 4 may also include a solar panel 12 for powering the sensor 8 and 10 and other components inside of and/or attached to the housing 6. The housing 6 may have a computer monitor 6a integrated therewith. The device 4 may also include a device 14 which may in the shape of a tube integrated with a handle. The device 14 may have an open end 14b, a closed end 14c, a body portion 14d, and an opening 14a in the body portion 14d.

FIG. 3 is a block diagram of various components of the apparatus 1 of FIG. 1A. The apparatus 1 may include a computer processor 18, a carbon monoxide level detector 20, a computer memory 22, and a battery 24, in addition to sensor 8, sensor 10, a computer monitor or display 6a, and a heart rate sensor 26. The components 18, 20, 22, 24, and 26 may be located within the housing 6 and/or may be attached to and/or integrated with the housing 6 shown in FIG. 1. The computer processor 18 may be electrically connected to and/or may communicate with components 20, 22, 24, 12, 8, 10, and 6a, in any known wired, wireless, optical, or any other known manner.

The device 4 may have an opening 16 which, in at least one embodiment leads to the carbon monoxide detector 20 which is part of the housing 6, and which is used to detect carbon monoxide in someone's breath. In the first state, shown in FIG. 1A, the shell of the body portion 14d covers the opening 16 of the carbon monoxide detector 20 of the housing 6, so that a person's breath cannot be analyzed by the internal carbon monoxide detector of the housing 16.

FIG. 1B shows a top, front, and left perspective view of the apparatus 1 of FIG. 1A shown in a second state. The device 14 has been pulled partially outwards from the housing 6 in the direction D1, from the first state of FIG. 1A to the second state of FIG. 1B. This causes the opening 14a of the device 14 to be aligned with the opening 16 of the carbon monoxide detector 20 of the housing 6. An individual can blow into the opening 14*b*, and the air passes through a hollow inner chamber of the body portion 14*d*, then through the opening 14*a* and into the opening 16 of the carbon monoxide detector 20 of the housing 6. The computer processor 18, in at least one embodiment, is programmed in accordance with computer software stored in the computer memory 22 to determine whether the breath received through opening 16 has a carbon monoxide content above a threshold and if so, the computer processor 18 is programmed to cause the sensor 8 to display the color red to indicate a concentration of carbon monoxide gas above a threshold. The sensor 8 may be a light emitting diode for example. The lighting of the sensor 8 red alerts a user of apparatus 1 to the presence of an unacceptable level of carbon monoxide, typically through the user's breath.

In at least one embodiment, as soon as user gets into an area or environment where user is exposed to a sufficient amount of carbon monoxide (CO), a display screen or LED of sensor 8 turns or lights red, such as in response to the computer processor 18, alerting a user of the presence of CO, then a user can check the amount of CO present in the body by blowing air into the opening 16, through the device 14. The sensor 8 may sense carbon monoxide without the user blowing into the device 14.

The opening 16 leading to internal carbon monoxide detector 20 in housing 6, allows the user to blow into the opening 14*b*, leading to an inner chamber of 14*d*, out through opening 14*a* in the second state of FIG. 1B, and into opening 16 to get a reading in ppm (parts per million) of the amount of carbon monoxide a person is being exposed from the computer monitor display 6*a* which may be located on the top face of the housing 6. The computer processor 18 may be programmed to produce a reading in ppm (parts per million), in response to signals received from the carbon monoxide level detector 20, and may cause the reading to be displayed on the computer monitor or display 6*a* or top face or surface monitor of the housing 6, about five to ten seconds from blowing into opening 14*b*, in the second state of FIG. 1B.

Sensor 10 shown in FIGS. 1A and 1B may be an audio alarm or a speaker. The computer processor 18 may be programmed by computer software stored in the computer memory 22 to cause an audio signal or sound to be emitted from the sensor or speaker 10 when the amount of carbon monoxide detected from a user breathing into end 14*b*, through inner chamber of 14*d*, through opening 14*a* and into opening 16, is at least fifty ppm (parts per million). The solar panel 12 of the apparatus 1 may recharge the battery 24 through the computer processor 18 and/or directly. The solar panel 12 may generally provide power to the components 8, 10, 6*a*, 18, 20, 22, and 24. The battery 24 may be stored in the housing 6 for providing power to components 8, 10, 12, 6*a*, 18, 20, 22, and 24 and internal circuitry of housing 6. The solar panel 12 helps the apparatus 1 to last for a period when the battery 24 runs down.

FIG. 2A shows a top, left, and front perspective view of the device 14. FIG. 2B shows a bottom, left, and rear perspective view of the tube having the handle of FIG. 2A. The device 14 is shaped as a hollow tube having a flared handle at an end 14*b*. The end 14*b* has an opening so that air can be blown into a hollow chamber of body portion 14*d* through end 14*b*, and then can flow out of the opening 14*a*. The end 14*c* is closed.

FIG. 4A shows a top, front, and left perspective view of an apparatus 100 in accordance with an embodiment of the present invention, with the apparatus 100 of FIG. 4A shown in a third state. FIG. 4B shows a top, front, and left perspective view of the apparatus 100 of FIG. 4A shown in a fourth state.

The apparatus 100 may be identical to the apparatus 1 of FIGS. 1A and 1B, except as will be described. The apparatus 100 may be a watch which may have a time display or monitor 118 which shows a time of 10:25 in both FIGS. 4A and 4B.

The apparatus 100 may have components 102, 108, 110, 112, and 114 which may be identical or substantially similar to components 2, 8, 10, 12, and 14 of the apparatus 1 of FIGS. 1A and 1B. The apparatus 100 may have a device 104 which may be identical to the device 4 of the apparatus 1, with the exception of time monitor or display 118, and watch knob 120, and in at least some embodiments, there may be some additional electronic components and/or other components which may be part of the housing 106 of FIG. 4A versus the housing 6 of FIG. 1A.

Similar or identical to FIG. 1A, the device 114 may be partially pulled outwards from the housing 106 to allow someone to blow air through the end 114*b*, into an inner chamber in the body portion 114*d*, out an opening 114*a* and into an opening 116 leading to a carbon monoxide detector inside the housing 106. If carbon monoxide is detected above a threshold, the sensor 108 may emit an audio alarm.

The wrist watch apparatus 100 may operate, in at least one embodiment, the same way as the apparatus 1, with regards to the number of sensors, such as sensors 108, 110, monitor 106*a* which may be identical and/or similar to sensors 8, 10, and monitor 6*a*. The apparatus 100 may include a known knob or dial to control the watch time display 118.

The device 104 may include the components shown in FIG. 3, attached to and/or integrated with the housing 106. The time monitor or display 118 may communicate with the computer processor 18 which may be inside of the housing 106. The watch knob 120 may also communicate with the computer processor 18 which may be inside of the housing 106.

The apparatus 1 and/or 100 helps to save lives by detecting carbon monoxide.

In at least one embodiment, the sensor 8 may be a carbon monoxide detector which displays the color red as soon as a sufficient level of Carbon Monoxide is detected as determined by the computer processor 18 programmed by the computer memory 22. The display of the color red by sensor 8 alerts the user to the presence of an unacceptably high level of CO in the environment or area where the user is. In at least one embodiment, after a user sees the sensor 8 light red, the user can now check the amount of CO present in the user's body by pulling the device 14 from the state of FIG. 1A to the state of FIG. 1B. Alternatively, the device 14 may be oriented with respect to the opening 16 to push the device 14 to allow air to be blown into device 14, into opening 16 of the carbon monoxide level detector 20. With the device 14 in the state of FIG. 1B, a user may blow into the inner chamber within device 14, into opening 16 of the internal carbon monoxide level detector 20. The computer processor 18 receives one or more signals related to the level of carbon monoxide and, in at least one embodiment, causes a reading to be displayed on the computer monitor 6*a* within seconds. In at least one embodiment, the computer processor 18 may be programmed by computer software stored in the computer memory 22 to cause the sensor or speaker 10 to emit an audio alarm or sound when the user's CO level as determined by the carbon monoxide level detector 20 and the computer processor 18, gets to fifty ppm (parts per million). In at least one embodiment, the sensor 8 includes its own carbon monoxide detector, and the sensor 8 or the sensor 10 may provide signals to the computer processor 18 which cause the audio alarm to go off, without the need for someone to blow into the device 14, opening 16, and into the carbon monoxide detector 20.

The heart rate sensor 26, in at least one embodiment, is located opposite to the monitor 6*a*, so that the heart rate sensor 26 will be against a user's skin who is wearing the apparatus 1. The heart rate sensor 26 monitors SpO2 (peripheral capillary oxygen saturation, an estimate of amount of oxygen in the blood) and heart rate of a user, and provides signals to the computer processor 18 indicating heart rate and SpO2 levels. The computer processor 18 causes a sound or alarm to be emitted, such as from the sensor 10, when heart rate is less than a lower limit, which may be sixty beats per minute or greater than an upper limit, which may be one hundred beats per minute, wherein these limits may be stored in the computer memory 22. The computer processor 18 may also cause a sound or audio alarm to be emitted from the sensor 10 when Spo2 (peripheral capillary oxygen saturation, an estimate of amount of oxygen in the blood) is less than a lower limit, such as ninety-two.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. An apparatus comprising:
a band; and
a first device configured to attach to a person's wrist using the band;
wherein the first device includes a first carbon monoxide level detector;
wherein the first device includes a housing and a second device configured to be moved with respect to the housing from a first state to a second state;
wherein in the first state a person cannot blow into the second device and cause a carbon monoxide level of the person's breath to be detected by the first carbon monoxide level detector;
wherein in the second state the person can blow into the second device and cause a carbon monoxide level of the person's breath to be detected by the first carbon monoxide level detector;
wherein in the first state the second device covers an opening leading to the first carbon monoxide level detector so that a person's breath cannot be analyzed by the first carbon monoxide level detector through the second device; and
wherein in the second state the second device does not cover the opening leading to the first carbon monoxide detector, so that a person's breath can be analyzed by the first carbon monoxide level detector through the second device.

2. The apparatus of claim 1 wherein the first device includes a second carbon monoxide level detector which is configured to detect a carbon monoxide level in ambient air.

3. The apparatus of claim 2 wherein
the first device includes a computer display which is configured to display a carbon monoxide level of the person's breath detected by the first carbon monoxide level detector; and
the computer display is also configured to display a carbon monoxide level in ambient air detected by the second carbon monoxide detector.

4. The apparatus of claim 2 wherein
the second carbon monoxide detector emits a colored light when a sufficient amount of carbon monoxide is detected.

5. The apparatus of claim 1 wherein
the first device includes a computer display which is configured to display a carbon monoxide level of the person's breath detected by the first carbon monoxide level detector.

6. The apparatus of claim 1 wherein the first device includes a heart rate monitor.

7. The apparatus of claim 1 wherein
the first device includes an SpO2 detector.

8. The apparatus of claim 1 wherein
the second device has a hollow inner chamber which can be accessed through an opening;
and wherein the second device is configured so that an individual can blow into the opening of the second device, and as a result air passes through the hollow inner chamber and into the opening of the carbon monoxide detector in the second state.

9. The apparatus of claim 8 wherein
the second device is shaped as a hollow tube having a flared handle at the opening of the second device.

10. The apparatus of claim 1 wherein
the second device is configured to be partially pulled outwards from the housing to change from the first state to the second state.

11. A method comprising the steps of:
attaching a first device to a person's wrist by a band; and
moving a second device with respect to a housing of the first device, from a first state to a second state;
wherein the first device includes a first carbon monoxide level detector;
wherein in the first state a person cannot blow into the second device and cause a carbon monoxide level of the person's breath to be detected by the first carbon monoxide level detector; and
wherein in the second state the person can blow into the second device and cause a carbon monoxide level of the person's breath to be detected by the first carbon monoxide level detector;
wherein in the first state the second device covers an opening leading to the first carbon monoxide level detector so that a person's breath cannot be analyzed by the first carbon monoxide level detector through the second device; and
wherein in the second state the second device does not cover the opening leading to the first carbon monoxide detector, so that a person's breath can be analyzed by the first carbon monoxide level detector through the second device.

12. The method of claim 11 wherein
the first device includes a second carbon monoxide level detector which is configured to detect a carbon monoxide level in ambient air.

13. The method of claim 12 wherein
the first device includes a computer display which is configured to display a carbon monoxide level of the person's breath detected by the first carbon monoxide level detector; and
the computer display is also configured to display a carbon monoxide level in ambient air detected by the second carbon monoxide detector.

14. The method of claim 12 wherein
the second carbon monoxide detector emits a colored light when a sufficient amount of carbon monoxide is detected.

15. The method of claim 11 wherein
the first device includes a computer display which is configured to display a carbon monoxide level of the person's breath detected by the first carbon monoxide level detector.

16. The method of claim 11 wherein the first device includes a heart rate monitor.

17. The method of claim 11 wherein the first device includes an SpO2 detector.

18. The method of claim 11 wherein
the second device has a hollow inner chamber which can be accessed through an opening;
and wherein the second device is configured so that an individual can blow into the opening of the second device, and as a result air passes through the hollow inner chamber and into the opening of the carbon monoxide detector in the second state.

19. The method of claim 11 wherein
the second device is configured to be partially pulled outwards from the housing to change from the first state to the second state.

20. The method of claim 11 wherein
the second device is shaped as a hollow tube having a flared handle at the opening of the second device.

* * * * *